(12) United States Patent
Choo et al.

(10) Patent No.: US 8,883,796 B2
(45) Date of Patent: Nov. 11, 2014

(54) BIPHENYL DERIVATIVES, PHARMACEUTICAL COMPOSITION COMPRISING THE SAME, AND PREPARATION METHOD THEREOF

(71) Applicant: Korea Institute of Science and Technology, Seoul (KR)

(72) Inventors: Hyunah Choo, Seoul (KR); Young-Jae Kim, Seoul (KR); Jeeyeon Kim, Seoul (KR); Mi Young Yeom, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/762,567

(22) Filed: Feb. 8, 2013

(65) Prior Publication Data

US 2014/0228568 A1 Aug. 14, 2014

(51) Int. Cl.
*A61K 31/4965* (2006.01)
*C07D 241/04* (2006.01)

(52) U.S. Cl.
CPC .................................. *C07D 241/04* (2013.01)
USPC ..................... 514/255.03; 544/392

(58) Field of Classification Search
CPC .................................................... C07D 241/04
See application file for complete search history.

(56) References Cited

U.S. PATENT DOCUMENTS 6,258,813 B1 * 7/2001 Arlt et al. ................. 514/252.11

FOREIGN PATENT DOCUMENTS

| WO | WO 97/29097 | 8/1997 |
| WO | WO 97/49695 | 12/1997 |
| WO | WO 99/24022 | 5/1999 |
| WO | WO 00/00472 | 1/2000 |
| WO | WO 03/048118 | 6/2003 |
| WO | WO 2010/012817 | 4/2010 |

OTHER PUBLICATIONS

American Chemical Society (ACS). STN CAS Registry Database. Updated through 2013.*
Organ, M.G., et al. "Solution-Phase Synthesis of an Aminomethyl-Substituted Biaryl Library via Sequential Amine N-Alkylation and Suzuki Cross-Coupling." J. Comb. Chem. (2001), 3, pp. 473-476.*
Mayo Clinic. "Depression (major depression)." (c) Feb. 12, 2012. Available from: < http://www.mayoclinic.com/health/depression/DS00175/DSECTION=prevention >.*
Rashbaum, RF. "Treatment Options for Neuropathic Pain." (c) 2013. Available from: < http://www.spine-health.com/treatment/pain-management/treatment-options-neuropathic-pain >.*
Kim, J., et al. "Aryl Biphenyl-3-ylmethylpiperazines as 5-HT7 Receptor Antagonists." ChemMedChem. (2013), vol. 8, pp. 1855-1864.*

* cited by examiner

*Primary Examiner* — Noble Jarrell
*Assistant Examiner* — John S Kenyon
(74) *Attorney, Agent, or Firm* — Staas & Halsey LLP

(57) ABSTRACT

Provided are biphenyl derivatives exhibiting activity towards central nervous system diseases by acting on the 5-HT$_7$ receptor, pharmaceutically acceptable salts thereof, a method for preparing the compounds and pharmaceutical compositions including the compounds as an active ingredient.

9 Claims, No Drawings

BIPHENYL DERIVATIVES, PHARMACEUTICAL COMPOSITION COMPRISING THE SAME, AND PREPARATION METHOD THEREOF

TECHNICAL FIELD

The present disclosure relates to biphenyl derivatives exhibiting activity towards central nervous system diseases by acting on the 5-$HT_7$ receptor, pharmaceutically acceptable salts thereof, a method for preparing the compounds and pharmaceutical compositions including the compounds as an active ingredient.

BACKGROUND

The neurotransmitter serotonin acts on the 14 different types of serotonin receptors located at various organs and thereby incurs various physiological phenomena. Among them, the 5-$HT_7$ receptor is the most recently cloned serotonin subtype receptor and is known to be distributed particularly at high densities in the hypothalamus, thalamus, hippocampus and cortex. Also, it is known to play important roles in thermoregulation, circadian rhythm, learning and memory, sleep, hippocampal signaling, or the like. It is also known that this receptor is involved in neurological disorders such as depression, migraine, anxiety, pain, particularly inflammatory pain and neuropathic pain, or the like.

Although there have been many efforts for development of antagonists or agonists of the 5-$HT_7$ receptor, very few selective 5-$HT_7$ receptor antagonists are reported. WO97/29097, WO97/49695 and WO03/048118 disclose sulfonamide-based antagonists, WO99/24022 and WO00/00472 disclose tetrahydroisoquinoline derivatives acting on the 5-$HT_7$ receptor, and WO 2010/012817 discloses 1-aryl-4-arylmethylpiperazine derivatives acting on the 5-$HT_7$ receptor.

However, there is still a need of a 5-$HT_7$ receptor regulator which is selective for the 5-$HT_7$ receptor, has a good pharmacodynamic profile, exhibits good absorption, distribution, metabolism and excretion (ADME), and is effective for neurological disorders such as depression, migraine, anxiety, pain, particularly inflammatory pain and neuropathic pain, etc. and diseases related with thermoregulation, circadian rhythm, sleep, smooth muscle, etc.

SUMMARY

The inventors of the present disclosure have made efforts to develop a novel compound acting on the 5-$HT_7$ receptor as a 5-$HT_7$ receptor regulator, which is effective for neurological disorders such as depression, migraine, anxiety, pain, particularly inflammatory pain and neuropathic pain, etc., thermoregulation, sleep, or the like by acting on the central nervous system or is effective for diseases related with smooth muscle, etc.

The present disclosure is directed to providing biphenyl derivatives of novel structures and pharmaceutically acceptable salts thereof.

The present disclosure is also directed to providing a method for preparing biphenyl compounds, including preparation of biphenyl aldehyde intermediates via Suzuki coupling and reductive amination of the biphenyl aldehydes with various arylpiperzines.

The present disclosure is also directed to providing pharmaceutical compositions acting on the 5-$HT_7$ serotonin receptor, which include the biphenyl compounds or the pharmaceutically acceptable salts thereof as an active ingredient.

The present disclosure is also directed to providing drugs for preventing or treating neurological disorders such as depression, migraine, anxiety, pain, particularly inflammatory pain and neuropathic pain, etc. and diseases related with thermoregulation, circadian rhythm, sleep or smooth muscle, which include the biphenyl compounds or the pharmaceutically acceptable salts thereof as an active ingredient.

In an aspect of the present disclosure, there is provided a biphenyl compound represented by Chemical Formula 1, which acts on the 5-$HT_7$ serotonin receptor and exhibits effect for neurological disorders such as depression, migraine, anxiety, pain, particularly inflammatory pain and neuropathic pain, etc. and diseases related with thermoregulation, circadian rhythm, sleep or smooth muscle, a method for preparing the compound and a pharmaceutical composition including the compound.

[Chemical Formula 1]

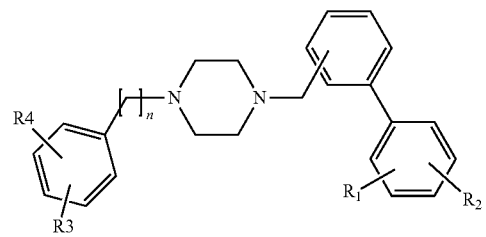

In Chemical Formula 1, each of $R_1$ and $R_2$, which are the same or different, is independently selected from hydrogen, halogen, alkyl, alkoxy, aryloxy and nitro; each of $R_3$ and $R_4$, which are the same or different, is independently selected from hydrogen, halogen, alkyl, alkoxy, aryloxy, nitro and phenyl; and n is 0 or 1.

In another general aspect, there is provided a pharmaceutical composition for preventing or treating a disease regulated by the action of the 5-$HT_7$ receptor selected from depression, migraine, anxiety, inflammatory pain, neuropathic pain, thermoregulatory disorder, insomnia and smooth muscle disorder, which includes the biphenyl derivative according to the present disclosure or a pharmaceutically acceptable salt thereof.

In another general aspect, there is provided a method for preparing the biphenyl derivative according to the present disclosure, including: (a) preparing a biphenyl aldehyde intermediate by Suzuki coupling an aryl boronic acid with bromobenzene aldehyde; and (b) preparing the biphenyl derivative according to the present disclosure by reductive aminating the biphenyl aldehyde intermediate with an arylpiperazine.

DETAILED DESCRIPTION OF EMBODIMENTS

The advantages, features and aspects of the present disclosure will become apparent from the following description of the embodiments with reference to the accompanying drawings, which is set forth hereinafter.

In an aspect of the present disclosure, there is provided a biphenyl derivative represented by the following chemical formula:

[Chemical Formula 1]

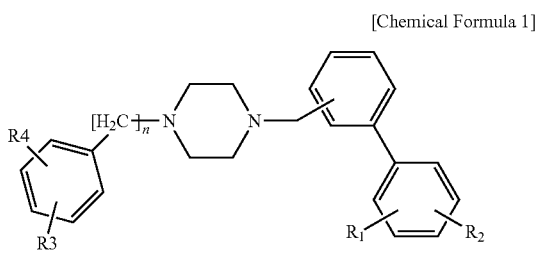

wherein each of $R_1$ and $R_2$, which are the same or different, is independently selected from hydrogen, halogen, alkyl, alkoxy, aryloxy and nitro; each of $R_3$ and $R_4$, which are the same or different, is independently selected from hydrogen, halogen, alkyl, alkoxy, aryloxy, nitro and phenyl; and n is 0 or 1.

In an exemplary embodiment, the biphenyl derivative has a structure of Chemical Formula 2 or Chemical Formula 3:

[Chemical Formula 2]

[Chemical Formula 3]

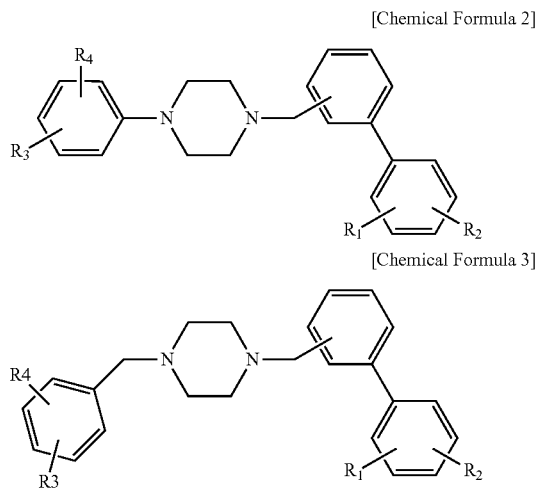

In another exemplary embodiment, the biphenyl derivative represented by Chemical Formula 2 has a structure of Chemical Formula 4 or Chemical Formula 5:

[Chemical Formula 4]

[Chemical Formula 5]

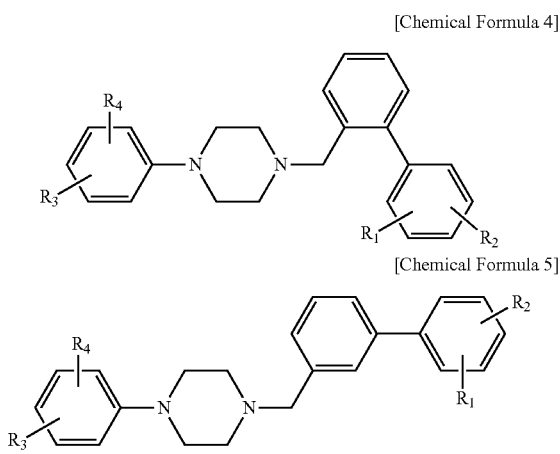

In another exemplary embodiment, each of $R_1$ and $R_2$, which are the same or different, is independently selected from hydrogen, halogen, $C_1$-$C_6$ alkoxy and $C_1$-$C_6$ alkyl; and each of $R_3$ and $R_4$, which are the same or different, is independently selected from hydrogen, halogen, $C_1$-$C_6$ alkoxy, phenoxy, $C_1$-$C_6$ alkyl and halogenated $C_1$-$C_6$ alkyl.

In another exemplary embodiment, each of $R_1$ and $R_2$, which are the same or different, is independently selected from hydrogen, fluoro, chloro, methyl and methoxy; and each of $R_3$ and $R_4$, which are the same or different, is independently selected from hydrogen, fluoro, chloro, methoxy, ethoxy, isopropoxy, phenoxy, methyl, isopropyl and trifluoromethyl.

In another exemplary embodiment, (A) $R_1$ is hydrogen and $R_2$ is selected from hydrogen, halogen, $C_1$-$C_6$ alkyl and $C_1$-$C_6$ alkoxy; and (B) (i) if $R_3$ is hydrogen, $R_4$ is selected from hydrogen, halogen, $C_1$-$C_6$ alkoxy, phenoxy, $C_1$-$C_6$ alkyl and halogenated $C_1$-$C_6$ alkyl, or (ii) each of $R_3$ and $R_4$ is $C_1$-$C_6$ alkoxy or $C_1$-$C_6$ alkyl.

In another exemplary embodiment, (A) $R_1$ is hydrogen and $R_2$ is selected from fluoro, chloro, methyl and methoxy; and (B) (i) if $R_3$ is hydrogen, $R_4$ is selected from hydrogen, fluoro, chloro, methoxy, ethoxy, isopropoxy, phenoxy, methyl, isopropyl and trifluoromethyl, or (ii) each of $R_3$ and $R_4$ is methoxy or methyl.

In another exemplary embodiment, the biphenyl derivative is selected from:
1-(biphenyl-2-ylmethyl)-4-phenylpiperazine;
1-(biphenyl-2-ylmethyl)-4-(2-fluorophenyl)piperazine;
1-(biphenyl-2-ylmethyl)-4-(3-fluorophenyl)piperazine;
1-(biphenyl-2-ylmethyl)-4-(4-fluorophenyl)piperazine;
1-(biphenyl-2-ylmethyl)-4-(2-chlorophenyl)piperazine;
1-(biphenyl-2-ylmethyl)-4-(3-chlorophenyl)piperazine;
1-(biphenyl-2-ylmethyl)-4-(4-chlorophenyl)piperazine;
1-(biphenyl-2-ylmethyl)-4-(2-methoxyphenyl)piperazine;
1-(biphenyl-2-ylmethyl)-4-(2-ethoxyphenyl)piperazine;
1-(biphenyl-2-ylmethyl)-4-(2-isopropoxyphenyl)piperazine;
1-(biphenyl-2-ylmethyl)-4-(3-methoxyphenyl)piperazine;
1-(biphenyl-2-ylmethyl)-4-(4-methoxyphenyl)piperazine;
1-(biphenyl-2-ylmethyl)-4-(3,4-dimethoxyphenyl)piperazine;
1-(biphenyl-2-ylmethyl)-4-(3,5-dimethoxyphenyl)piperazine;
1-(biphenyl-2-ylmethyl)-4-(2-phenoxyphenyl)piperazine;
1-(biphenyl-2-ylmethyl)-4-(2-methylphenyl)piperazine;
1-(biphenyl-2-ylmethyl)-4-(3-methylphenyl)piperazine;
1-(biphenyl-2-ylmethyl)-4-(4-methylphenyl)piperazine;
1-(biphenyl-2-ylmethyl)-4-(2,3-dimethylphenyl)piperazine;
1-(biphenyl-2-ylmethyl)-4-(2,4-dimethylphenyl)piperazine;
1-(biphenyl-2-ylmethyl)-4-(2,5-dimethylphenyl)piperazine;
1-(biphenyl-2-ylmethyl)-4-(3,5-dimethylphenyl)piperazine;
1-(biphenyl-2-ylmethyl)-4-(2-isopropylphenyl)piperazine;
1-(biphenyl-2-ylmethyl)-4-(biphenyl-2-yl)piperazine;
1-(biphenyl-2-ylmethyl)-4-(3-(trifluoromethyl)phenyl)piperazine;
1-(2'-fluorobiphenyl-2-ylmethyl)-4-(2-methoxyphenyl)piperazine;
1-(2'-chlorobiphenyl-2-ylmethyl)-4-(2-methoxyphenyl)piperazine;
1-(3'-chlorobiphenyl-2-ylmethyl)-4-(2-methoxyphenyl)piperazine;
1-(4'-chlorobiphenyl-2-ylmethyl)-4-(2-methoxyphenyl)piperazine;
1-(2'-methoxybiphenyl-2-ylmethyl)-4-(2-methoxyphenyl)piperazine;
1-(3'-methoxybiphenyl-2-ylmethyl)-4-(2-methoxyphenyl)piperazine;

1-(4'-methoxybiphenyl-2-ylmethyl)-4-(2-methoxyphenyl)piperazine;
1-(2'-methylbiphenyl-2-ylmethyl)-4-(2-methoxyphenyl)piperazine;
1-(biphenyl-3-ylmethyl)-4-phenylpiperazine;
1-(biphenyl-3-ylmethyl)-4-(2-fluorophenyl)piperazine;
1-(biphenyl-3-ylmethyl)-4-(3-fluorophenyl)piperazine;
1-(biphenyl-3-ylmethyl)-4-(4-fluorophenyl)piperazine;
1-(biphenyl-3-ylmethyl)-4-(2-chlorophenyl)piperazine;
1-(biphenyl-3-ylmethyl)-4-(3-chlorophenyl)piperazine;
1-(biphenyl-3-ylmethyl)-4-(4-chlorophenyl)piperazine;
1-(biphenyl-3-ylmethyl)-4-(2-methoxyphenyl)piperazine;
1-(biphenyl-3-ylmethyl)-4-(3-methoxyphenyl)piperazine;
1-(biphenyl-3-ylmethyl)-4-(4-methoxyphenyl)piperazine;
1-(biphenyl-3-ylmethyl)-4-(3,4-dimethoxyphenyl)piperazine;
1-(biphenyl-3-ylmethyl)-4-(2-ethoxyphenyl)piperazine;
1-(biphenyl-3-ylmethyl)-4-(2-methylphenyl)piperazine;
1-(biphenyl-3-ylmethyl)-4-(3-methylphenyl)piperazine;
1-(biphenyl-3-ylmethyl)-4-(4-methylphenyl)piperazine;
1-(biphenyl-3-ylmethyl)-4-(2,3-dimethylphenyl)piperazine;
1-(biphenyl-3-ylmethyl)-4-(2,5-dimethylphenyl)piperazine;
1-(biphenyl-3-ylmethyl)-4-(2,4-dimethylphenyl)piperazine;
1-(biphenyl-3-ylmethyl)-4-(3,5-dimethylphenyl)piperazine;
1-(biphenyl-3-ylmethyl)-4-(3-(trifluoromethyl)phenyl)piperazine;
1-(2'-fluorobiphenyl-3-ylmethyl)-4-(2-methoxyphenyl)piperazine;
1-(2'-chlorobiphenyl-3-ylmethyl)-4-(2-methoxyphenyl)piperazine;
1-(2'-methoxybiphenyl-3-ylmethyl)-4-(2-methoxyphenyl)piperazine; and
1-(2'-methylbiphenyl-3-ylmethyl)-4-(2-methoxyphenyl)piperazine.

In another aspect of the present disclosure, there is provided a pharmaceutical composition for preventing or treating a disease regulated by the action of the 5-HT$_7$ receptor selected from depression, migraine, anxiety, inflammatory pain, neuropathic pain, thermoregulatory disorder, insomnia and smooth muscle disorder, which comprises the biphenyl derivative according to the present disclosure or a pharmaceutically acceptable salt thereof.

In another aspect of the present disclosure, there is provided a method for preparing a biphenyl derivative represented by Chemical Formula 2, comprising: (a) preparing a biphenyl aldehyde intermediate represented by Chemical Formula 8 by Suzuki coupling an aryl boronic acid represented by Chemical Formula 6 with bromobenzene aldehyde represented by Chemical Formula 7; and (b) preparing the compound represented by Chemical Formula 2 by reductive aminating the biphenyl aldehyde intermediate with an arylpiperazine represented by Chemical Formula 9:

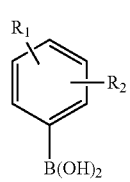
[Chemical Formula 6]

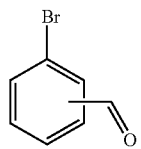
[Chemical Formula 7]

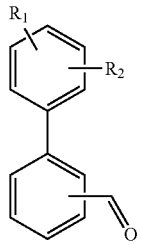
[Chemical Formula 8]

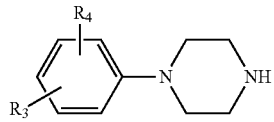
[Chemical Formula 9]

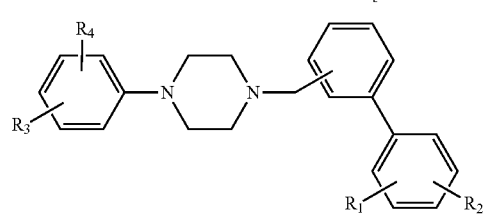
[Chemical Formula 2]

wherein each of $R_1$ and $R_2$, which are the same or different, is independently selected from hydrogen, halogen, alkyl, alkoxy, aryloxy and nitro; and each of $R_3$ and $R_4$, which are the same or different, is independently selected from hydrogen, halogen, alkyl, alkoxy, aryloxy and nitro.

In an exemplary embodiment, (A) $R_1$ is hydrogen and $R_2$ is selected from fluoro, chloro, methyl and methoxy; and (B) (i) if $R_3$ is hydrogen, $R_4$ is selected from hydrogen, fluoro, chloro, methoxy, ethoxy, isopropoxy, phenoxy, methyl, isopropyl and trifluoromethyl, or (ii) each of $R_3$ and $R_4$ is methoxy or methyl.

The biphenyl compound represented by Chemical Formula 1 according to the present disclosure may be prepared into a pharmaceutically acceptable salt according to a method commonly employed in the art. For example, a pharmaceutically acceptable addition salt may be formed using a nontoxic inorganic acid such as hydrochloric acid, bromic acid, sulfonic acid, amidosulfuric acid, phosphoric acid and nitric acid or a nontoxic organic acid such as acetic acid, propionic acid, succinic acid, glycolic acid, stearic acid, lactic acid, tartaric acid, citric acid, p-toluenesulfonic acid and methanesulfonic acid.

Hereinafter, the substituents used to define the biphenyl compound represented by Chemical Formula 1 according to the present disclosure will be described in detail.

As used herein, "alkyl" includes linear, branched and cyclic carbon chains having 1 to 6 carbon atoms. Specifically, the alkyl may be methyl, ethyl, n-propyl, isopropyl, n-butyl, isobutyl, tert-butyl, cyclopentyl, cyclohexyl, or the like.

As used herein, "alkoxy" means alkyl bonded to oxygen, wherein the alkyl is the same as defined above. In the biphenyl compound represented by Chemical Formula 1, each of $R_1$ and $R_2$ may be specifically hydrogen, halogen, $C_1$-$C_6$ alkyl or $C_1$-$C_6$ alkoxy.

More specifically, in the biphenyl compound represented by Chemical Formula 1, each of $R_1$ and $R_2$ may be hydrogen, fluorine, chlorine, methyl, dimethyl, methoxy, ethoxy, isopropoxy, dimethoxy, nitro or phenoxy.

Specific examples of the biphenyl compound represented by Chemical Formula 1 are as follows.

Compound 1: 1-(biphenyl-2-ylmethyl)-4-phenylpiperazine

Compound 2: 1-(biphenyl-2-ylmethyl)-4-(2-fluorophenyl)piperazine

Compound 3: 1-(biphenyl-2-ylmethyl)-4-(3-fluorophenyl)piperazine

Compound 4: 1-(biphenyl-2-ylmethyl)-4-(4-fluorophenyl)piperazine

Compound 5: 1-(biphenyl-2-ylmethyl)-4-(2-chlorophenyl)piperazine

Compound 6: 1-(biphenyl-2-ylmethyl)-4-(3-chlorophenyl)piperazine

Compound 7: 1-(biphenyl-2-ylmethyl)-4-(4-chlorophenyl)piperazine

Compound 8: 1-(biphenyl-2-ylmethyl)-4-(2-methoxyphenyl)piperazine

Compound 9: 1-(biphenyl-2-ylmethyl)-4-(2-ethoxyphenyl)piperazine

Compound 10: 1-(biphenyl-2-ylmethyl)-4-(2-isopropoxyphenyl)piperazine

Compound 11: 1-(biphenyl-2-ylmethyl)-4-(3-methoxyphenyl)piperazine

Compound 12: 1-(biphenyl-2-ylmethyl)-4-(4-methoxyphenyl)piperazine

Compound 13: 1-(biphenyl-2-ylmethyl)-4-(3,4-dimethoxyphenyl)piperazine

Compound 14: 1-(biphenyl-2-ylmethyl)-4-(3,5-dimethoxyphenyl)piperazine

Compound 15: 1-(biphenyl-2-ylmethyl)-4-(2-phenoxyphenyl)piperazine

Compound 16: 1-(biphenyl-2-ylmethyl)-4-(2-methylphenyl)piperazine

Compound 17: 1-(biphenyl-2-ylmethyl)-4-(3-methylphenyl)piperazine

Compound 18: 1-(biphenyl-2-ylmethyl)-4-(4-methylphenyl)piperazine

Compound 19: 1-(biphenyl-2-ylmethyl)-4-(2,3-dimethylphenyl)piperazine

Compound 20: 1-(biphenyl-2-ylmethyl)-4-(2,4-dimethylphenyl)piperazine

Compound 21: 1-(biphenyl-2-ylmethyl)-4-(2,5-dimethylphenyl)piperazine

Compound 22: 1-(biphenyl-2-ylmethyl)-4-(3,5-dimethylphenyl)piperazine

Compound 23: 1-(biphenyl-2-ylmethyl)-4-(2-isopropylphenyl)piperazine

Compound 24: 1-(biphenyl-2-ylmethyl)-4-(biphenyl-2-yl)piperazine

Compound 25: 1-(biphenyl-2-ylmethyl)-4-(3-(trifluoromethyl)phenyl)piperazine

Compound 26: 1-(2'-fluorobiphenyl-2-ylmethyl)-4-(2-methoxyphenyl)piperazine

Compound 27: 1-(2'-chlorobiphenyl-2-ylmethyl)-4-(2-methoxyphenyl)piperazine

Compound 28: 1-(3'-chlorobiphenyl-2-ylmethyl)-4-(2-methoxyphenyl)piperazine

Compound 29: 1-(4'-chlorobiphenyl-2-ylmethyl)-4-(2-methoxyphenyl)piperazine

Compound 30: 1-(2'-methoxybiphenyl-2-ylmethyl)-4-(2-methoxyphenyl)piperazine

Compound 31: 1-(3'-methoxybiphenyl-2-ylmethyl)-4-(2-methoxyphenyl)piperazine

Compound 32: 1-(4'-methoxybiphenyl-2-ylmethyl)-4-(2-methoxyphenyl)piperazine

Compound 33: 1-(2'-methylbiphenyl-2-ylmethyl)-4-(2-methoxyphenyl)piperazine

Compound 34: 1-(biphenyl-3-ylmethyl)-4-phenylpiperazine

Compound 35: 1-(biphenyl-3-ylmethyl)-4-(2-fluorophenyl)piperazine

Compound 36: 1-(biphenyl-3-ylmethyl)-4-(3-fluorophenyl)piperazine

Compound 37: 1-(biphenyl-3-ylmethyl)-4-(4-fluorophenyl)piperazine

Compound 38: 1-(biphenyl-3-ylmethyl)-4-(2-chlorophenyl)piperazine

Compound 39: 1-(biphenyl-3-ylmethyl)-4-(3-chlorophenyl)piperazine

Compound 40: 1-(biphenyl-3-ylmethyl)-4-(4-chlorophenyl)piperazine

Compound 41: 1-(biphenyl-3-ylmethyl)-4-(2-methoxyphenyl)piperazine

Compound 42: 1-(biphenyl-3-ylmethyl)-4-(3-methoxyphenyl)piperazine

Compound 43: 1-(biphenyl-3-ylmethyl)-4-(4-methoxyphenyl)piperazine

Compound 44: 1-(biphenyl-3-ylmethyl)-4-(3,4-dimethoxyphenyl)piperazine

Compound 45: 1-(biphenyl-3-ylmethyl)-4-(2-ethoxyphenyl)piperazine

Compound 46: 1-(biphenyl-3-ylmethyl)-4-(2-methylphenyl)piperazine

Compound 47: 1-(biphenyl-3-ylmethyl)-4-(3-methylphenyl)piperazine

Compound 48: 1-(biphenyl-3-ylmethyl)-4-(4-methylphenyl)piperazine

Compound 49: 1-(biphenyl-3-ylmethyl)-4-(2,3-dimethylphenyl)piperazine

Compound 50: 1-(biphenyl-3-ylmethyl)-4-(2,5-dimethylphenyl)piperazine

Compound 51: 1-(biphenyl-3-ylmethyl)-4-(2,4-dimethylphenyl)piperazine

Compound 52: 1-(biphenyl-3-ylmethyl)-4-(3,5-dimethylphenyl)piperazine

Compound 53: 1-(biphenyl-3-ylmethyl)-4-(3-(trifluoromethyl)phenyl)piperazine

Compound 54: 1-(2'-fluorobiphenyl-3-ylmethyl)-4-(2-methoxyphenyl)piperazine

Compound 55: 1-(2'-chlorobiphenyl-3-ylmethyl)-4-(2-methoxyphenyl)piperazine

Compound 56: 1-(2'-methoxybiphenyl-3-yl methyl)-4-(2-methoxyphenyl)piperazine

Compound 57: 1-(2'-methylbiphenyl-3-ylmethyl)-4-(2-methoxyphenyl)piperazine

The present disclosure further provides a method for preparing the biphenyl compound represented by Chemical Formula 1. The preparation method according to the present disclosure may be expressed by Scheme 1. In Scheme 1, each of $R_1$ and $R_2$ is the same as defined in Chemical Formula 1.

[Scheme 1]

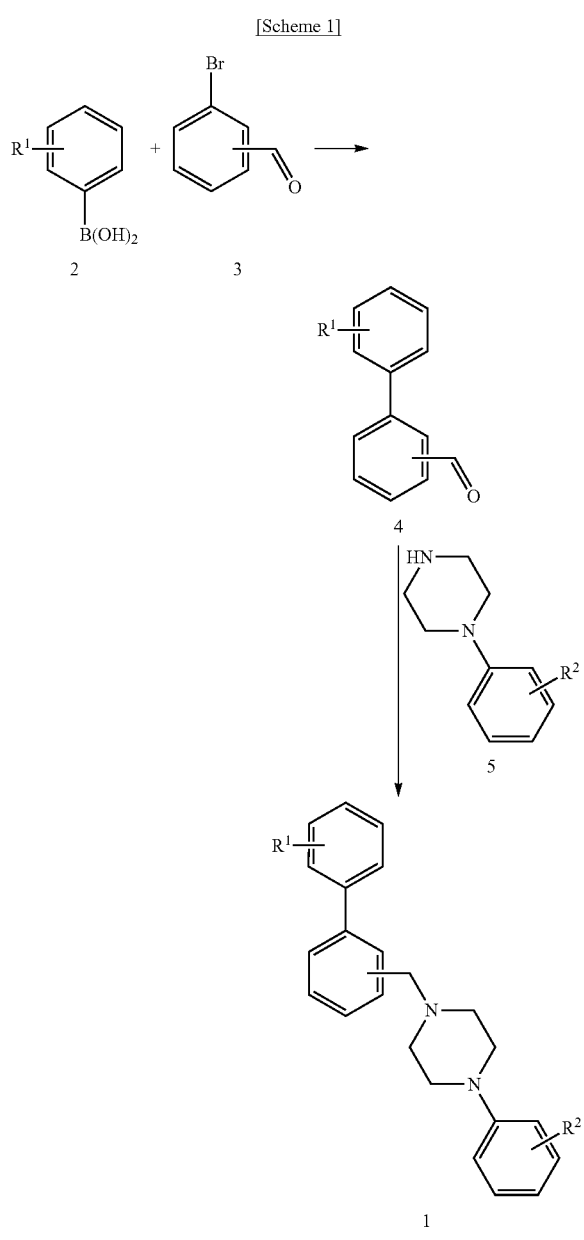

First, a biphenyl aldehyde is obtained from Suzuki coupling of an arylboronic acid (2) with bromobenzene aldehyde (3).

Various catalysts including Pd may be used for the Suzuki coupling reaction. In the following examples, Pd(PPh$_3$)$_4$ was mainly used. As for a reaction solvent, a commonly used organic solvent may be used. Specifically, N,N-dimethylformamide, acetonitrile, tetrahydrofuran, etc. may be used. In the following examples, N,N-dimethylformamide was mainly used. Reaction temperature may be maintained at 50-200° C. Reaction time is about 3-24 hours, specifically 7-10 hours.

After the reaction is completed, the reaction mixture is extracted using an organic solvent and purified by column chromatography to obtain the biphenyl compound (4). This biphenyl compound is reductively aminated with an arylpiperazine (5) to obtain the biphenyl derivative represented by Chemical Formula 1, which is a target compound.

As a reducing agent used in the reaction, various reducing agents such as NaBH(OAc)$_3$, NaBH$_3$CN, etc. may be used. In the following examples, NaBH(OAc)$_3$ was mainly used. Reaction temperature may be around room temperature. The reaction temperature may be specifically 10-500° C., more specifically 20-30° C. Reaction time may be 3-24 hours, specifically 4-8 hours. After the reaction is completed, the reaction mixture is extracted using an organic solvent to obtain the compound represented by Chemical Formula 1.

The present disclosure also provides a pharmaceutical composition for prevention and treatment of diseases, comprising the biphenyl compound represented by Chemical Formula 1 or a pharmaceutically acceptable salt thereof as an active ingredient.

The pharmaceutical composition of the present disclosure may be prepared into formulations suitable for oral or parenteral administration using the biphenyl compound represented by Chemical Formula 1 or a pharmaceutically acceptable salt thereof together with a commonly used carrier, adjuvant, diluent, etc. For oral administration, it may be prepared into tablet, capsule, solution, syrup, suspension, etc. And, for parenteral administration, it may be prepared into formulation for intraabdominal, subcutaneous, intramuscular or transdermal injection.

The pharmaceutical composition of the present disclosure may be administered at a dosage of 0.01-1,000 mg/day for an adult based on the regulator acting on the 5-HT$_7$ serotonin receptor. The administration dosage may be changed depending on the age, body weight, sex and health condition of a patient and the severity of disease. Depending on the discretion of a doctor or a pharmacist, the administration may be made once or several times a day with regular time intervals.

Accordingly, the present disclosure provides a medical use of the biphenyl compound represented by Chemical Formula 1, a pharmaceutically acceptable thereof or a pharmaceutical composition comprising same for prevention and treatment of diseases.

Since the biphenyl compound of the present disclosure functions as a regulator acting on the 5-HT$_7$ serotonin receptor, the present disclosure covers a medical use for prevention and treatment of neurological disorders such as depression, migraine, anxiety, pain, particularly inflammatory pain and neuropathic pain, etc. and diseases related with thermoregulation, circadian rhythm, sleep or smooth muscle.

The present disclosure further provides a method for preventing or treating diseases by administering the biphenyl compound represented by Chemical Formula 1 or a pharmaceutically acceptable salt thereof to a patient.

EXAMPLES

Hereinafter, the present disclosure will be described in more detail through examples and test examples. However, the following examples and test examples are for illustrative purposes only and not intended to limit the scope of this disclosure.

Examples

Biphenyl-2-carbaldehyde

2-Bromobenzaldehyde (315 μL, 2.70 mmol), phenylboronic acid (395 mg, 3.24 mmol), Pd(PPh$_3$)$_4$ (31 mg, 0.027 mmol) and Na$_2$CO$_3$ (430 mg, 4.05 mmol) were dissolved in N,N-dimethylformamide (20 mL) in a reaction vessel and refluxed at 160° C. for 6 hours. After the reaction was completed, the reaction mixture was diluted with EtOAc and saturated NaHCO₃ solution was added. The organic layer obtained by extracting the aqueous layer with EtOAc was dried with anhydrous MgSO₄ and then filtered. The filtrate was concentrated under reduced pressure and the concentrate was purified by column chromatography (hexane:diethyl ether=8:1) to obtain 369 mg of the target compound (2.03 mmol, 75.0%).

$^1$H NMR (400 MHz, CDCl₃) δ 10.0 (s, 1H), 8.05 (dd, J=6.6 Hz, J=1.2 Hz, 1H), 7.65 (dd, J=6.1 Hz, J=1.4 Hz, 1H), 7.51-7.46 (m, 5H), 7.40 (dd, J=5.9 Hz, J=2.0 Hz, 2H).

1-Bromo-2-phenoxybenzene

2-Bromophenol (1.22 mL, 11.6 mmol), phenylboronic acid (2.8 g, 23.1 mmol), Cu(OAc)₂ (4.2 g, 23.1 mmol) and pyridine (4.66 mL, 57.8 mmol) were dissolved in dichloromethane (100 mL) in a reaction vessel holding 1 g of 4 Å M.S. and stirred at room temperature for 18 hours. After the reaction was completed, the reaction mixture was diluted with dichloromethane and filtered through Celite. The filtrate was extracted with 1 N NaOH and brine, and the organic layer was dried with anhydrous MgSO₄ and filtered again. The filtrate was concentrated under reduced pressure) to obtain 436 mg of the target compound (1.75 mmol, 15.1%).

$^1$H NMR (300 MHz, CDCl₃) δ 7.63 (dd, J=8.1 Hz, J=1.8 Hz, 1H), 7.36-7.23 (m, 3H), 7.13-7.08 (m, 1H), 7.04-6.94 (m, 4H).

1-(2-Phenoxyphenyl)piperazine

1-Bromo-2-phenoxybenzene (432 mg, 1.73 mmol), piperazine (299 mg, 3.47 mmol), Pd₂(dba)₃ (48 mg, 0.052 mmol), BINAP (54 mg, 0.087 mmol) and NaOt-Bu (249 mg, 2.60 mmol) were dissolved in toluene (10 mL) in a reaction vessel and refluxed at 100° C. for 20 hours. After the reaction was completed, the reaction mixture was diluted with EtOAc and filtered through Celite. The filtrate was concentrated under reduced pressure and the concentrate was purified by column chromatography (MC:mixture solution (MC:MeOH:H₂O:NH₃=80:20:1:1)=6:1) to obtain 283 mg of the target compound (1.11 mmol, 64.3%).

$^1$H NMR (300 MHz, CDCl₃) δ 7.31-7.24 (m, 2H), 7.14-6.92 (m, 7H), 3.07 (t, J=4.5 Hz, 4H), 2.84 (t, J=4.5 Hz, 4H).

Compound 1:
1-(biphenyl-2-ylmethyl)-4-phenylpiperazine

1-Phenylpiperazine (266 mg, 1.64 mmol) was dissolved in methanol (7 mL) in a reaction vessel and, after adding biphenyl-2-carbaldehyde (150 mg, 0.82 mmol), the mixture was stirred at room temperature for 2 hours. 2 hours later, NaBH(OAc)₃ (529 mg, 2.46 mmol) was added and the mixture was further stirred for 8 hours. After the reaction was completed, the reaction solution was diluted with dichloromethane and saturated NaHCO₃ solution was added. After extraction, organic layer was dried with anhydrous MgSO₄ and then filtered. The filtrate was concentrated and the concentrate was purified by column chromatography (hexane:diethyl ether=8:1) to obtain 50 mg of the target compound (0.15 mmol, 18.3%).

$^1$H NMR (300 MHz, CDCl₃) δ 7.76 (d, J=6.9 Hz, 1H), 7.64-7.44 (m, 8H), 7.21-7.01 (m, 4H), 3.65 (s, 2H), 3.20 (brs, 4H), 2.71 (brs, 4H).

Compound 2: 1-(biphenyl-2-ylmethyl)-4-(2-fluorophenyl)piperazine 20 mg of the target compound (0.06 mmol, 7.32%) was obtained using 1-(2-fluorophenyl)piperazine (296 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.76 (d, J=6.9 Hz, 1H), 7.64-7.44 (m, 8H), 7.21-7.01 (m, 4H), 3.65 (s, 2H), 3.20 (brs, 4H), 2.71 (brs, 4H).

Compound 3: 1-(biphenyl-2-ylmethyl)-4-(3-fluorophenyl)piperazine 80 mg of the target compound (0.23 mmol, 28.0%) was obtained using 1-(3-fluorophenyl)piperazine (296 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.60-7.57 (m, 1H), 7.50-7.30 (m, 8H), 7.24-7.16 (m, 1H), 6.69-6.51 (m, 3H), 3.50 (s, 2H), 3.17 (brt, J=4.8 Hz, 4H), 2.53 (brt, J=5.1 Hz, 4H).

Compound 4: 1-(biphenyl-2-ylmethyl)-4-(4-fluorophenyl)piperazine 96 mg of the target compound (0.28 mmol, 34.0%) was obtained using 1-(4-fluorophenyl)piperazine (296 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.64-7.33 (m, 9H), 7.05-6.89 (m, 4H), 3.65 (s, 2H), 3.13 (brt, J=4.8 Hz, 4H), 2.68 (brt, J=4.8 Hz, 4H).

Compound 5: 1-(biphenyl-2-ylmethyl)-4-(2-chlorophenyl)piperazine 60 mg of the target compound (0.17 mmol, 20.7%) was obtained using 1-(2-chlorophenyl)piperazine hydrochloride (382 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.60 (d, J=6.6 Hz, 1H), 7.52-7.31 (m, 9H), 7.27-7.21 (m, 1H), 7.06 (dd, J=8.1 Hz, J=1.5 Hz, 1H), 6.98 (td, J=7.5 Hz, J=1.5 Hz, 1H), 3.53 (s, 2H), 3.05 (brs, 4H), 2.59 (brs, 4H).

Compound 6: 1-(biphenyl-2-ylmethyl)-4-(3-chlorophenyl)piperazine 31.7 mg of the target compound (0.09 mmol, 10.6%) was obtained using 1-(3-chlorophenyl)piperazine hydrochloride (382 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.56-7.23 (m, 9H), 7.12 (t, J=8.1 Hz, 1H), 6.84-6.72 (m, 3H), 3.46 (s, 2H), 3.11 (brt, J=4.8 Hz, 4H), 2.48 (brt, J=4.8 Hz, 4H).

Compound 7: 1-(biphenyl-2-ylmethyl)-4-(4-chlorophenyl)piperazine 20 mg of the target compound (0.06 mmol, 7.3%) was obtained using 1-(4-chlorophenyl)piperazine hydrochloride (382 mg, 1.64 mmol), biphenyl-2-carbaldehyde (150 mg, 0.82 mmol) and NaBH(OAc)₃ (529 mg, 2.46 mmol) according to the synthesis method of Compound 1.

$^1$H NMR (300 MHz, CDCl₃) δ 7.63-7.23 (m, 11H), 6.89-6.85 (m, 2H), 3.54 (s, 2H), 3.16 (brt, J=5.1 Hz, 4H), 2.57 (brt, J=5.1 Hz, 4H).

Compound 8: 1-(biphenyl-2-ylmethyl)-4-(2-methoxyphenyl)piperazine 74 mg of the target compound (0.21 mmol, 37.5%) was obtained using 1-(2-methoxyphenyl)piperazine (211 mg, 1.10 mmol), biphenyl-2-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.59 (d, J=6.8 Hz, 1H), 7.48-7.29 (m, 8H), 7.04-6.86 (m, 4H), 3.86 (s, 3H), 3.51 (s, 2H), 3.06 (brs, 4H), 2.06 (brs, 4H).

Compound 9: 1-(biphenyl-2-ylmethyl)-4-(2-ethoxyphenyl)piperazine 112.3 mg of the target compound (0.30 mmol, 36.6%) was obtained using 1-(2-ethoxyphenyl)piperazine hydrochloride (400 mg, 1.65 mmol), biphenyl-2-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.59 (d, J=6.8 Hz, 1H), 7.48-7.29 (m, 8H), 7.04-6.86 (m, 4H), 3.86 (s, 3H), 3.51 (s, 2H), 3.06 (brs, 4H), 2.06 (brs, 4H).

Compound 10: 1-(biphenyl-2-ylmethyl)-4-(2-isopropoxyphenyl)piperazine 108 mg of the target compound (0.28 mmol, 50.8%) was obtained using 1-(2-isopropoxyphenyl)piperazine (240 mg, 1.09 mmol), biphenyl-2-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.58 (d, J=9.0 Hz, 1H), 7.42-7.24 (m, 8H), 6.92-6.82 (m, 4H), 4.57 (septet, J=6.3 Hz, 1H), 3.47 (s, 2H), 3.05 (brs, 4H), 2.53 (brs, 4H), 1.32 (s, 3H), 1.29 (s, 3H).

Compound 11: 1-(biphenyl-2-ylmethyl)-4-(3-methoxyphenyl)piperazine 124 mg of the target compound (0.35 mmol, 42.7%) was obtained using 1-(3-methoxyphenyl)piperazine (315 mg, 1.64 mmol), biphenyl-2-carbaldehyde (150 mg, 0.82 mmol) and NaBH(OAc)$_3$ (529 mg, 2.46 mmol) according to the synthesis method of Compound 1.

Compound 12: 1-(biphenyl-2-ylmethyl)-4-(4-methoxyphenyl)piperazine 128.8 mg of the target compound (0.36 mmol, 65.3%) was obtained using 1-(4-methoxyphenyl)piperazine (212 mg, 1.10 mmol), biphenyl-2-carbaldehyde (100 mg, 0.55 mmol) and NaBH(OAc)$_3$ (355 mg, 1.65 mmol) according to the synthesis method of Compound 1.

Compound 13: 1-(biphenyl-2-ylmethyl)-4-(3,4-dimethoxyphenyl)piperazine 167.9 mg of the target compound (0.43 mmol, 78.6%) was obtained using 1-(3,4-dimethoxyphenyl)piperazine (245 mg, 1.10 mmol), biphenyl-2-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.60 (d, J=6.3 Hz, 1H), 7.45-7.30 (m, 8H), 6.82 (d, J=8.7 Hz, 1H), 6.59 (brd, J=2.4 Hz, 1H), 6.47 (dd, J=8.7 Hz, J=2.7 Hz, 1H), 3.89 (s, 3H), 3.87 (s, 3H), 3.54 (s, 2H), 3.09 (brt, J=4.5 Hz, 4H), 2.57 (brt, J=4.5 Hz, 4H).

Compound 14: 1-(biphenyl-2-ylmethyl)-4-(3,5-dimethoxyphenyl)piperazine

The target compound was obtained according to the synthesis method of Compound 1.

Compound 15: 1-(biphenyl-2-ylmethyl)-4-(2-phenoxyphenyl)piperazine 151 mg of the target compound (0.36 mmol, 64.9%) was obtained using 1-(2-phenoxyphenyl)piperazine (277 mg, 1.09 mmol), biphenyl-2-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.52-7.49 (m, 1H), 7.39-7.22 (m, 10H), 7.08-6.87 (m, 7H), 3.36 (s, 2H), 3.06 (brs, 4H), 2.35 (brs, 4H).

Compound 16: 1-(biphenyl-2-ylmethyl)-4-(2-methylphenyl)piperazine 140.7 mg of the target compound (0.41 mmol, 74.7%) was obtained using 1-(2-methylphenyl)piperazine (193.8 mg, 1.1 mmol), biphenyl-2-carbaldehyde (100 mg, 0.55 mmol) and NaBH(OAc)$_3$ (355 mg, 1.65 mmol) according to the synthesis method of Compound 1.

Compound 17: 1-(biphenyl-2-ylmethyl)-4-(3-methylphenyl)piperazine 153.8 mg of the target compound (0.45 mmol, 54.9%) was obtained using 1-(3-methylphenyl)piperazine (289 mg, 1.64 mmol), biphenyl-2-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.82-7.79 (m, 1H), 7.67-7.51 (m, 8H), 7.36 (t, J=7.5 Hz, 1H), 6.95-6.88 (m, 3H), 3.70 (s, 2H), 3.34 (brt, J=5.1 Hz, 4H), 2.73 (brt, J=4.8 Hz, 4H), 2.54 (s, 3H).

Compound 18: 1-(biphenyl-2-ylmethyl)-4-(4-methylphenyl)piperazine 70.4 mg of the target compound (0.21 mmol, 47.7%) was obtained using 1-(4-methylphenyl)piperazine (155 mg, 0.88 mmol), biphenyl-2-carbaldehyde (80 mg, 0.44 mmol) and NaBH(OAc)$_3$ (284 mg, 1.32 mmol) according to the synthesis method of Compound 1.

$^1$H NMR (300 MHz, CDCl$_3$) δ 7.75-7.70 (m, 1H), 7.61-7.41 (m, 8H), 7.32-7.28 (m, 2H), 7.18-7.09 (m, 2H), 3.64 (s, 2H), 3.03 (brt, J=4.5 Hz, 4H), 2.68 (brs, 4H), 2.43 (s, 3H).

Compound 19: 1-(biphenyl-2-ylmethyl)-4-(2,3-dimethylphenyl)piperazine 52.7 mg of the target compound (0.15 mmol, 18.3%) was obtained using 1-(2,3-dimethylphenyl)piperazine (312 mg, 1.64 mmol), biphenyl-2-carbaldehyde (150 mg, 0.82 mmol) and NaBH(OAc)$_3$ (529 mg, 2.46 mmol) according to the synthesis method of Compound 1.

¹H NMR (300 MHz, CDCl₃) δ 7.57 (d, J=6.9 Hz, 1H), 7.44-7.03 (m, 7H), 7.05 (t, J=7.5 Hz, 2H), 6.88 (t, J=7.2 Hz, 2H), 3.47 (s, 2H), 2.84 (brt, J=4.5 Hz, 4H), 2.52 (brs, 4H), 2.24 (s, 3H), 2.17 (s, 3H).

Compound 20: 1-(biphenyl-2-ylmethyl)-4-(2,4-dimethylphenyl)piperazine 201.6 mg of the target compound (0.57 mmol, 69.0%) was obtained using 1-(2,4-dimethylphenyl)piperazine (312 mg, 1.64 mmol), biphenyl-2-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.78-7.75 (m, 1H), 7.62-7.42 (m, 8H), 7.14-7.06 (m, 3H), 3.67 (s, 2H), 3.01 (brt, J=3.9 Hz, 4H), 2.69 (brs, 4H), 2.42 (s, 3H), 2.41 (s, 3H).

Compound 21: 1-(biphenyl-2-ylmethyl)-4-(2,5-dimethylphenyl)piperazine 35.8 mg of the target compound (0.10 mmol, 12.2%) was obtained using 1-(2,5-dimethylphenyl)piperazine (312 mg, 1.64 mmol), biphenyl-2-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.59-7.26 (m, 7H), 7.05 (d, J=7.5 Hz, 1H), 6.82-6.76 (m, 2H), 3.47 (s, 2H), 2.84 (brt, J=4.5 Hz, 4H), 2.52 (brs, 4H), 2.24 (s, 3H), 2.17 (s, 3H).

Compound 22: 1-(biphenyl-2-ylmethyl)-4-(3,5-dimethylphenyl)piperazine 58 mg of the target compound (0.16 mmol, 19.5%) was obtained using 1-(3,5-dimethylphenyl)piperazine (312 mg, 1.64 mmol), biphenyl-2-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.57-7.54 (m, 1H), 7.47-7.20 (m, 8H), 6.53-6.50 (m, 3H), 3.45 (s, 2H), 3.10 (brt, J=4.8 Hz, 4H), 2.49 (brt, J=4.8 Hz, 4H), 2.26 (s, 6H).

Compound 23: 1-(biphenyl-2-ylmethyl)-4-(2-isopropylphenyl)piperazine 100 mg of the target compound (0.27 mmol, 49.1%) was obtained using 1-(2-isopropylphenyl)piperazine (223 mg, 1.09 mmol), biphenyl-2-carbaldehyde (100 mg, 0.55 mmol) and NaBH(OAc)₃ (355 mg, 1.65 mmol) according to the synthesis method of Compound 1.
¹H NMR (300 MHz, CDCl₃) δ 7.58 (dd, J=6.9 Hz, J=1.8 Hz, 1H), 7.44-7.22 (m, 9H), 7.15-7.05 (m, 3H), 3.48-3.46 (m, 3H), 2.84 (brt, J=4.8 Hz, 4H), 2.52 (brs, 4H), 1.18 (s, 3H), 1.16 (s, 3H).

Compound 24: 1-(biphenyl-2-ylmethyl)-4-(biphenyl-2-yl)piperazine 148 mg of the target compound (0.37 mmol, 66.5%) was obtained using 1-(biphenyl-2-yl)piperazine (260 mg, 1.09 mmol), biphenyl-2-carbaldehyde (100 mg, 0.55 mmol) and NaBH(OAc)₃ (355 mg, 1.65 mmol) according to the synthesis method of Compound 1.
¹H NMR (300 MHz, CDCl₃) δ 7.50-7.48 (m, 2H), 7.43-7.21 (m, 14H), 7.07-6.99 (m, 2H), 3.36 (s, 2H), 2.79 (brt, J=4.5 Hz, 4H), 2.26 (brs, 4H).

Compound 25: 1-(biphenyl-2-ylmethyl)-4-(3-(trifluoromethyl)phenyl)piperazine 19.2 mg of the target compound (0.05 mmol, 5.6%) was obtained using 1-(3-trifluoromethylphenyl)piperazine hydrochloride (437 mg, 1.64 mmol), biphenyl-2-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.57-7.54 (m, 1H), 7.41-7.25 (m, 9H), 7.07-7.00 (m, 3H), 3.47 (s, 2H), 3.17 (brt, J=5.1 Hz, 4H), 2.51 (brs, 4H).

Compound 26: 1-(2'-fluorobiphenyl-2-ylmethyl)-4-(2-methoxyphenyl)piperazine 379 mg of the target compound (1.01 mmol, 32.5%) was obtained using 1-(2-methoxyphenyl)piperazine (1.2 g, 6.20 mmol), 2'-fluorobiphenyl-2-carbaldehyde (620 mg, 3.10 mmol) and NaBH(OAc)₃ (2.0 g, 9.30 mmol) according to the synthesis method of Compound 1.
¹H NMR (300 MHz, CDCl₃) δ 7.64 (dd, J=6.8 Hz, J=1.5 Hz, 1H), 7.44-7.11 (m, 7H), 7.03-6.92 (m, 3H), 6.86 (d, J=7.9 Hz, 1H), 3.85 (s, 3H), 3.48 (s, 2H), 3.00 (brs, 4H), 2.52 (brs, 4H).

Compound 27: 1-(2'-chlorobiphenyl-2-ylmethyl)-4-(2-methoxyphenyl)piperazine 69 mg of the target compound (0.18 mmol, 21.7%) was obtained using 1-(2-methoxyphenyl)piperazine (311 mg, 1.62 mmol), 2'-chlorobiphenyl-2-carbaldehyde (175 mg, 0.81 mmol) and NaBH(OAc)₃ (523 mg, 2.43 mmol) according to the synthesis method of Compound 1.
¹H NMR (400 MHz, CDCl₃) δ 7.59 (dd, J=7.6 Hz, J=0.8 Hz, 1H), 7.46-7.24 (m, 6H), 7.17 (d, J=7.6 Hz, 1H), 6.99-6.88 (m, 3H), 6.82 (d, J=7.8 Hz, 1H), 3.81 (s, 3H), 3.44 (d, J=13.5 Hz, 1H), 3.28 (d, J=13.5 Hz, 1H), 2.96 (brs, 4H), 2.47 (brs, 4H).

Compound 28: 1-(3'-chlorobiphenyl-2-ylmethyl)-4-(2-methoxyphenyl)piperazine 250 mg of the target compound (0.64 mmol, 40.5%) was obtained using 1-(2-methoxyphenyl)piperazine (603 mg, 3.14 mmol), 3'-chlorobiphenyl-2-carbaldehyde (340 mg, 1.57 mmol) and NaBH(OAc)₃ (1.0 g, 4.71 mmol) according to the synthesis method of Compound 1.
¹H NMR (300 MHz, CDCl₃) δ 7.71 (brs, 1H), 7.56-7.52 (m, 1H), 7.43-7.30 (m, 6H), 7.06-6.92 (m, 3H), 6.90 (d, J=7.5 Hz, 1H), 3.89 (s, 3H), 3.47 (s, 2H), 3.10 (brs, 4H), 2.65 (brs, 4H).

Compound 29: 1-(4'-chlorobiphenyl-2-ylmethyl)-4-(2-methoxyphenyl)piperazine 215 mg of the target compound (0.55 mmol, 42.4%) was obtained using 1-(2-methoxyphenyl)piperazine (497 mg, 2.58 mmol), 4'-chlorobiphenyl-2-carbaldehyde (280 mg, 1.29 mmol) and NaBH(OAc)₃ (832 mg, 3.87 mmol) according to the synthesis method of Compound 1.
¹H NMR (300 MHz, CDCl₃) δ 7.61 (dd, J=6.4 Hz, J=2.3 Hz, 1H), 7.51-7.31 (m, 7H), 7.09-6.98 (m, 3H), 6.92 (d, J=7.2 Hz, 1H), 3.91 (s, 3H), 3.52 (s, 2H), 3.12 (brs, 4H), 2.66 (brs, 4H).

Compound 30: 1-(2'-methoxybiphenyl-2-yl methyl)-4-(2-methoxyphenyl)piperazine 382 mg of the target compound (0.98 mmol, 59.6%) was obtained using 1-(2-methoxyphenyl)piperazine (634 mg, 3.30 mmol), 2'-methoxybiphenyl-2-carbaldehyde (350 mg, 1.65 mmol) and NaBH(OAc)$_3$ (1.1 g, 4.95 mmol) according to the synthesis method of Compound 1.

$^1$H NMR (400 MHz, CDCl$_3$) δ 7.62 (dd, J=7.6 Hz, J=1.0 Hz, 1H), 7.36-7.25 (m, 3H), 7.19-7.15 (m, 2H), 7.00-6.89 (m, 5H), 6.80 (d, J=7.6 Hz, 1H), 3.79 (s, 3H), 3.71 (s, 3H), 3.46 (d, J=13.4 Hz, 1H), 3.33 (d, J=13.4 Hz, 1H), 2.98 (brs, 4H), 2.48 (brs, 4H).

Compound 31: 1-(3'-methoxybiphenyl-2-yl methyl)-4-(2-methoxyphenyl)piperazine 176 mg of the target compound (0.45 mmol, 96.4%) was obtained using 1-(2-methoxyphenyl)piperazine (181 mg, 0.94 mmol), 3'-methoxybiphenyl-2-carbaldehyde (100 mg, 0.47 mmol) and NaBH(OAc)$_3$ (303 mg, 1.41 mmol) according to the synthesis method of Compound 1.

$^1$H NMR (300 MHz, CDCl$_3$) δ 7.55-7.53 (m, 1H), 7.34-7.26 (m, 4H), 7.03-6.80 (m, 7H), 3.80 (s, 6H), 3.48 (s, 2H), 3.02 (brs, 4H), 2.58 (brs, 4H).

Compound 32: 1-(4'-methoxybiphenyl-2-ylmethyl)-4-(2-methoxyphenyl)piperazine 149 mg of the target compound (0.38 mmol, 81.6%) was obtained using 1-(2-methoxyphenyl)piperazine (181 mg, 0.94 mmol), 4'-methoxybiphenyl-2-carbaldehyde (100 mg, 0.47 mmol) and NaBH(OAc)$_3$ (303 mg, 1.41 mmol) according to the synthesis method of Compound 1.

$^1$H NMR (300 MHz, CDCl$_3$) δ 7.53-7.51 (m, 1H), 7.38-7.24 (m, 5H), 6.95-6.87 (m, 5H), 6.80 (d, J=7.2 Hz, 1H) 3.80 (s, 3H), 3.79 (s, 3H), 3.46 (s, 2H), 3.02 (brs, 4H), 2.57 (brs, 4H).

Compound 33: 1-(2'-methylbiphenyl-2-ylmethyl)-4-(2-methoxyphenyl)piperazine 186 mg of the target compound (0.50 mmol, 97.9%) was obtained using 1-(2-methoxyphenyl)piperazine (196 mg, 1.02 mmol), 2'-methylbiphenyl-2-carbaldehyde (100 mg, 0.51 mmol) and NaBH(OAc)$_3$ (329 mg, 1.53 mmol) according to the synthesis method of Compound 1.

$^1$H NMR (300 MHz, CDCl$_3$) δ 7.58 (dd, J=7.5 Hz, J=1.2 Hz, 1H), 7.35-7.10 (m, 7H), 6.96-6.86 (m, 3H), 6.79 (d, J=7.5 Hz, 1H), 3.78 (s, 3H), 3.34 (d, J=13.5 Hz, 1H), 3.22 (d, J=13.5 Hz, 1H), 2.98 (brs, 4H), 2.47 (brs, 4H), 2.05 (s, 3H).

Compound 34: 1-(biphenyl-3-ylmethyl)-4-phenylpiperazine 48.6 mg of the target compound (0.15 mmol, 18.3%) was obtained using 1-phenylpiperazine (266 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.61-7.18 (m, 11H), 6.93-6.81 (m, 3H), 3.63 (s, 2H), 3.20 (brt, J=5.1 Hz, 4H), 2.64 (brt, J=5.1 Hz, 4H).

Compound 35: 1-(biphenyl-3-ylmethyl)-4-(2-fluorophenyl)piperazine 190.8 mg of the target compound (0.55 mmol, 67.2%) was obtained using 1-(2-fluorophenyl)piperazine (296 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.63-7.32 (m, 9H), 6.98-6.84 (m, 4H), 3.64 (s, 2H), 3.13 (brt, J=5.1 Hz, 4H), 2.65 (brt, J=5.1 Hz, 4H).

Compound 36: 1-(biphenyl-3-ylmethyl)-4-(3-fluorophenyl)piperazine 113.2 mg of the target compound (0.33 mmol, 59.4%) was obtained using 1-(3-fluorophenyl)piperazine (198 mg, 1.10 mmol), biphenyl-3-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.67-7.37 (m, 9H), 7.22 (q, J=7.2 Hz, 1H), 6.72-6.55 (m, 3H), 3.67 (s, 2H), 3.26 (brt, J=5.1 Hz, 4H), 2.67 (brt, J=4.8 Hz, 4H).

Compound 37: 1-(biphenyl-3-ylmethyl)-4-(4-fluorophenyl)piperazine 74.7 mg of the target compound (0.22 mmol, 26.8%) was obtained using 1-(4-fluorophenyl)piperazine (296 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.64-7.33 (m, 9H), 7.05-6.89 (m, 4H), 3.65 (s, 2H), 3.13 (brt, J=4.8 Hz, 4H), 2.68 (brt, J=4.8 Hz, 4H).

Compound 38: 1-(biphenyl-3-ylmethyl)-4-(2-chlorophenyl)piperazine 200.0 mg of the target compound (0.55 mmol, 67.2%) was obtained using 1-(2-chlorophenyl)piperazine hydrochloride (382 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.63-7.59 (m, 3H), 7.52-7.33 (m, 7H), 7.21 (t, J=8.1 Hz, 1H), 7.04 (dd, J=8.1 Hz, J=1.5 Hz, 1H), 6.96 (td, J=7.2 Hz, J=1.5 Hz, 1H), 3.66 (s, 2H), 3.09 (brs, 4H), 2.69 (brs, 4H).

Compound 39: 1-(biphenyl-3-ylmethyl)-4-(3-chlorophenyl)piperazine 11 mg of the target compound (0.03 mmol, 3.7%) was obtained using 1-(3-chlorophenyl)piperazine hydrochloride (382 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.63-7.58 (m, 3H), 7.52-7.32 (m, 6H), 7.15 (t, J=8.1 Hz, 1H), 6.86 (brt, J=2.1 Hz, 1H), 6.80-6.75 (m, 2H), 3.63 (s, 2H), 3.21 (brt, J=5.1 Hz, 4H), 2.63 (brt, J=5.1 Hz, 4H).

Compound 40: 1-(biphenyl-3-ylmethyl)-4-(4-chlorophenyl)piperazine 12 mg of the target compound (0.03 mmol, 4.03%) was obtained using 1-(4-chlorophenyl)piperazine hydrochloride (382 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.62-7.32 (m, 9H), 7.23-7.17 (m, 2H), 6.84-6.81 (m, 2H), 3.64 (s, 2H), 3.17 (brt, J=5.1 Hz, 4H), 2.64 (brt, J=5.1 Hz, 4H).

Compound 41: 1-(biphenyl-3-ylmethyl)-4-(2-methoxyphenyl)piperazine 47 mg of the target compound (0.13 mmol, 23.8%) was obtained using 1-(2-methoxyphenyl)piperazine (209 mg, 1.09 mmol), biphenyl-3-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.67-7.63 (m, 3H), 7.56-7.37 (m, 6H), 7.03-6.84 (m, 4H), 3.88 (s, 3H), 3.69 (s, 2H), 3.14 (brs, 4H), 2.74 (brs, 4H).

Compound 42: 1-(biphenyl-3-ylmethyl)-4-(3-methoxyphenyl)piperazine 126.1 mg of the target compound (0.35 mmol, 42.9%) was obtained using 1-(3-methoxyphenyl)piperazine (315 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.78-7.45 (m, 8H), 7.33-7.27 (m, 1H), 6.69-6.53 (m, 3H), 3.90 (s, 3H), 3.75 (s, 2H), 3.34 (brs, 4H), 2.76 (brs, 4H).

Compound 43: 1-(biphenyl-3-ylmethyl)-4-(4-methoxyphenyl)piperazine 128.2 mg of the target compound (0.36 mmol, 65.0%) was obtained using 1-(4-methoxyphenyl)piperazine (212 mg, 1.10 mmol), biphenyl-3-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.67-7.63 (m, 3H), 7.56-7.37 (m, 6H), 6.96-6.87 (m, 4H), 3.80 (s, 3H), 3.68 (s, 2H), 3.15 (brt, J=4.5 Hz, 4H), 2.70 (brt, J=4.8 Hz, 4H).

Compound 44: 1-(biphenyl-3-ylmethyl)-4-(3,4-dimethoxyphenyl)piperazine 166.8 mg of the target compound (0.43 mmol, 78.0%) was obtained using 1-(3,4-dimethoxyphenyl)piperazine (244.5 mg, 1.10 mmol), biphenyl-3-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.66-7.61 (m, 1H), 7.45-7.30 (m, 9H), 6.83-6.80 (m, 1H), 6.59-6.58 (m, 1H), 6.46 (dd, J=8.7 Hz, J=2.7 Hz, 1H), 3.98 (s, 3H), 3.89 (s, 3H), 3.54 (s, 2H), 3.10 (brs, 4H), 2.58 (brs, 4H).

Compound 45: 1-(biphenyl-3-ylmethyl)-4-(2-ethoxyphenyl)piperazine 48 mg of the target compound (0.13 mmol, 23.4%) was obtained using 1-(2-ethoxyphenyl)piperazine monohydrogen chloride (266 mg, 1.09 mmol), biphenyl-3-carbaldehyde (100 mg, 0.55 mmol) and NaBH(OAc)$_3$ (355 mg, 1.65 mmol) according to the synthesis method of Compound 1.

$^1$H NMR (300 MHz, CDCl$_3$) δ 7.62-7.60 (m, 3H), 7.51-7.31 (m, 6H), 6.97-6.81 (m, 4H), 4.04 (q, J=6.9 Hz, 2H), 3.64 (s, 2H), 3.13 (brs, 4H), 2.68 (brs, 4H), 1.43 (t, J=6.9 Hz, 3H).

Compound 46: 1-(biphenyl-3-ylmethyl)-4-(2-methylphenyl)piperazine 41.2 mg of the target compound (0.12 mmol, 14.7%) was obtained using 1-(2-methylphenyl)piperazine (289 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.73-7.70 (m, 3H), 7.61-7.43 (m, 6H), 7.30-7.03 (m, 4H), 3.74 (s, 2H), 3.04 (brt, J=4.5 Hz, 4H), 2.75 (brs, 4H), 2.40 (s, 3H).

Compound 47: 1-(biphenyl-3-ylmethyl)-4-(3-methylphenyl)piperazine 118.7 mg of the target compound (0.35 mmol, 42.3%) was obtained using 1-(3-methylphenyl)piperazine (289 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.80-7.77 (m, 3H), 7.69-7.47 (m, 6H), 7.31 (t, J=7.8 Hz, 1H), 6.91-6.83 (m, 3H), 3.78 (s, 2H), 3.36 (brt, J=4.8 Hz, 4H), 2.79 (brt, J=4.8 Hz, 4H), 2.48 (s, 3H).

Compound 48: 1-(biphenyl-3-ylmethyl)-4-(4-methylphenyl)piperazine 54.3 mg of the target compound (0.16 mmol, 36.4%) was obtained using 1-(4-methylphenyl)piperazine (154.8 mg, 0.88 mmol), biphenyl-3-carbaldehyde (80 mg, 0.44 mmol) and NaBH(OAc)$_3$ (283.8 mg, 1.32 mmol) according to the synthesis method of Compound 1.

$^1$H NMR (300 MHz, CDCl$_3$) δ 7.71-7.69 (m, 1H), 7.58-7.40 (m, 8H), 7.19 (d, J=8.1 Hz, 2H), 6.95 (d, J=8.4 Hz, 2H), 3.61 (s, 2H), 3.22 (brt, J=5.1 Hz, 4H), 2.65 (brt, J=5.1 Hz, 4H), 2.40 (s, 3H).

Compound 49: 1-(biphenyl-3-ylmethyl)-4-(2,3-dimethylphenyl)piperazine 58.3 mg of the target compound (0.16 mmol, 20.0%) was obtained using 1-(2,3-dimethylphenyl)piperazine (312 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.63-7.34 (m, 9H), 7.09-6.88 (m, 3H), 3.65 (s, 2H), 2.92 (brt, J=4.8 Hz, 4H), 2.66 (brs, 4H), 2.26 (s, 3H), 2.21 (s, 3H).

Compound 50: 1-(biphenyl-3-ylmethyl)-4-(2,5-dimethylphenyl)piperazine 62.1 mg of the target compound (0.17 mmol, 21.2%) was obtained using 1-(2,5-dimethylphenyl)piperazine (312 mg, 1.64 mmol), biphenyl-3-carbaldehyde (150 mg, 0.82 mmol) and NaBH(OAc)$_3$ (529 mg, 2.46 mmol) according to the synthesis method of Compound 1.

$^1$H NMR (300 MHz, CDCl$_3$) δ 7.79-7.46 (m, 9H), 7.22-6.93 (m, 3H), 3.80 (s, 2H), 3.08 (brt, J=4.8 Hz, 4H), 2.80 (brs, 4H), 2.45-2.38 (m, 6H).

Compound 51: 1-(biphenyl-3-ylmethyl)-4-(2,4-dimethylphenyl)piperazine 156.4 mg of the target compound (0.44 mmol, 53.7%) was obtained using 1-(2,4-dimethylphenyl)piperazine (312 mg, 1.64 mmol), biphenyl-3-carbaldehyde (150 mg, 0.82 mmol) and NaBH(OAc)$_3$ (529 mg, 2.46 mmol) according to the synthesis method of Compound 1.

¹H NMR (300 MHz, CDCl₃) δ 7.87-7.53 (m, 9H), 7.22-7.16 (m, 3H), 3.85 (s, 2H), 3.14 (brt, J=4.8 Hz, 4H), 2.86 (brs, 4H), 2.51 (s, 3H), 2.50 (s, 3H).

Compound 52: 1-(biphenyl-3-ylmethyl)-4-(3,5-dimethylphenyl)piperazine 138.6 mg of the target compound (0.39 mmol, 47.6%) was obtained using 1-(3,5-dimethylphenyl)piperazine (312 mg, 1.64 mmol), biphenyl-3-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.81-7.78 (m, 3H), 7.70-7.48 (m, 6H), 6.74-6.70 (m, 3H), 3.79 (s, 2H), 3.36 (brt, J=4.8 Hz, 4H), 2.79 (brs, 4H), 2.45 (s, 6H).

Compound 53: 1-(biphenyl-3-ylmethyl)-4-(3-(trifluoromethyl)phenyl)piperazine 14.0 mg of the target compound (0.04 mmol, 4.3%) was obtained using 1-(3-trifluorophenyl)piperazine hydrochloride (437 mg, 1.64 mmol), biphenyl-3-carbaldehyde (150 mg, 0.82 mmol) and NaBH(OAc)₃ (529 mg, 2.46 mmol) according to the synthesis method of Compound 1.
¹H NMR (300 MHz, CDCl₃) δ 7.62-7.30 (m, 10H), 7.10-7.02 (m, 3H), 3.64 (s, 2H), 3.25 (brt, J=4.8 Hz, 4H), 2.64 (brt, J=4.8 Hz, 4H)

Compound 54: 1-(2'-fluorobiphenyl-3-ylmethyl)-4-(2-methoxyphenyl)piperazine 164 mg of the target compound (0.44 mmol, 87.1%) was obtained using 1-(2-methoxyphenyl)piperazine (192 mg, 1.00 mmol), 2'-fluorobiphenyl-3-carbaldehyde (100 mg, 0.50 mmol) and NaBH(OAc)₃ (322 mg, 1.50 mmol) according to the synthesis method of Compound 1.
¹H NMR (300 MHz, CDCl₃) δ 7.61 (brs, 1H), 7.52-7.41 (m, 4H), 7.36-7.30 (m, 1H), 7.26-7.15 (m, 2H), 7.06-6.95 (m, 3H), 6.91 (dd, J=8.1 Hz, J=1.2 Hz, 1H), 3.88 (s, 3H), 3.70 (s, 2H), 3.16 (brs, 4H), 2.75 (brs, 4H).

Compound 55: 1-(2'-chlorobiphenyl-3-ylmethyl)-4-(2-methoxyphenyl)piperazine 61 mg of the target compound (0.16 mmol, 33.7%) was obtained using 1-(2-methoxyphenyl)piperazine (177 mg, 0.92 mmol), 2'-chlorobiphenyl-3-carbaldehyde (100 mg, 0.46 mmol) and NaBH(OAc)₃ (297 mg, 1.38 mmol) according to the synthesis method of Compound 1.
¹H NMR (300 MHz, CDCl₃) δ 7.46-7.44 (m, 2H), 7.42-7.23 (m, 6H), 7.00-6.87 (m, 3H), 6.84 (d, J=7.8 Hz, 1H), 3.83 (s, 3H), 3.65 (s, 2H), 3.10 (brs, 4H), 2.70 (brs, 4H).

Compound 56: 1-(2'-methoxybiphenyl-3-yl methyl)-4-(2-methoxyphenyl)piperazine 103 mg of the target compound (0.27 mmol, 56.4%) was obtained using 1-(2-methoxyphenyl)piperazine (181 mg, 0.94 mmol), 2'-methoxybiphenyl-3-carbaldehyde (100 mg, 0.47 mmol) and NaBH(OAc)₃ (303 mg, 1.41 mmol) according to the synthesis method of Compound 1.
¹H NMR (300 MHz, CDCl₃) δ 7.51 (brs, 1H), 7.45-7.27 (m, 5H), 7.04-6.87 (m, 5H), 6.83 (dd, J=7.8 Hz, J=0.9 Hz, 1H), 3.82 (s, 3H), 3.78 (s, 3H), 3.63 (s, 2H), 3.09 (brs, 4H), 2.69 (brs, 4H).

Compound 57: 1-(2'-methylbiphenyl-3-ylmethyl)-4-(2-methoxyphenyl)piperazine 77 mg of the target compound (0.21 mmol, 40.5%) was obtained using 1-(2-methoxyphenyl)piperazine (196 mg, 1.02 mmol), 2'-methylbiphenyl-3-carbaldehyde (100 mg, 0.51 mmol) and NaBH(OAc)₃ (329 mg, 1.53 mmol) according to the synthesis method of Compound 1.
¹H NMR (300 MHz, CDCl₃) δ 7.36-7.30 (m, 3H), 7.26-7.19 (m, 5H), 6.99-6.81 (m, 4H), 3.82 (s, 3H), 3.62 (s, 2H), 3.09 (brs, 4H), 2.69 (brs, 4H), 2.27 (s, 3H).

Formulation Examples

The novel compound represented by Chemical Formula 1 according to the present disclosure can be prepared into various formulations depending on purposes. Some formulation examples comprising the compound represented by Chemical Formula 1 are provided for illustrative purposes but they do not limit the scope of the present disclosure.

Formulation Example 1

Tablet (Direct Compression)

5.0 mg of the active ingredient was sieved, mixed with 14.1 mg of lactose, 0.8 mg of crospovidone USNF and 0.1 mg of magnesium stearate, and then compressed into a tablet.

Formulation Example 2

Tablet (Wet Granulation)

5.0 mg of the active ingredient was sieved and mixed with 16.0 mg of lactose and 4.0 mg of starch. After adding an adequate amount of a solution of 0.3 mg of Polysorbate 80 dissolved in pure water, the mixture was granulated. After drying and sieving, the granule was mixed with 2.7 mg of colloidal silicon dioxide and 2.0 mg of magnesium stearate. The granule was compressed into a tablet.

Formulation Example 3

Powder and Capsule 5.0 mg of the active ingredient was sieved and mixed with 14.8 mg of lactose, 10.0 mg of polyvinylpyrrolidone and 0.2 mg of magnesium stearate. The mixture was filled in hard No. 5 gelatin capsule using an appropriate apparatus.

Formulation Example 4

Injection

An injection was prepared using 100 mg of the active ingredient as well as 180 mg of mannitol, 26 mg of Na₂HPO₄.12H₂O and 2974 mg distilled water.

Test Example

% inhibition at 10 μM and binding affinity ($K_i$) of the novel compound represented by the Chemical Formula 1 according to the present disclosure for the 5-HT$_7$ serotonin receptor were measured as follows.

Test Example 1

Binding Affinity for 5-HT$_7$ Serotonin Receptor

Human recombinant 5-HT$_7$ receptor expressed in CHO cells was used. A reaction mixture (final concentration 0.25 mL) prepared from 1 nM [$^3$H]LSD, 5-HT$_7$ receptor membrane (15 μg/well), test compound of various concentrations and 50 mM Tris-HCl buffer (pH 7.4) containing 10 mM MgCl$_2$ and 0.1 mM EDTA was incubated at 25° C. for 90 minutes. After the incubation, reaction was terminated by rapid filtration through Whatman GF/C glass fiber filter previously soaked in 0.3% polyethyleneimine using a Brandel harvester and washed with cold 50 mM Tris-HCl buffer. The filter was covered with MeltiLex, sealed in a sample bag and dried in an oven. Counting was carried out using MicroBeta (Wallac). Nonspecific binding was measured in the presence of 0.5 μM mianserin. The $K_i$ value of the test compound was obtained from nonlinear regression analysis (GraphPad Prism Program, San Diego, USA) of isotherms obtained by repeating experiments 3 times in duplicate test tubes at 10-11 varied concentrations.

The % inhibition at 10 μM and binding affinity ($K_i$) of the novel compound according to the present disclosure for the 5-HT$_7$ serotonin receptor are given in Table 1.

TABLE 1

| Test compounds | % inhibition (10 μM) | $K_i$ (nM) |
|---|---|---|
| Compound 1 | 59.7 | 537.0 |
| Compound 8 | 95.1 | 431.9 |
| Compound 9 | 86.2 | 192.0 |
| Compound 21 | 93.8 | 658.0 |
| Compound 22 | 84.0 | 367.3 |
| Compound 23 | 87.0 | 273.7 |
| Compound 24 | 93.8 | 255.5 |
| Compound 25 | 95.9 | 64.0 |
| Compound 36 | 91.3 | 79.0 |
| Compound 38 | 88.3 | 66.0 |
| Compound 47 | 95.4 | 15.0 |

As described above, since the biphenyl compound represented by Chemical Formula 1 according to the present disclosure or a pharmaceutically acceptable salt thereof exhibits superior activity for the 5-HT$_7$ serotonin receptor, it is useful for treatment and prevention of neurological disorders such as depression, migraine, anxiety, pain, particularly inflammatory pain and neuropathic pain, etc. and diseases related with thermoregulation, circadian rhythm, sleep or smooth muscle.

While the present disclosure has been described with respect to the specific embodiments, it will be apparent to those skilled in the art that various changes and modifications may be made without departing from the spirit and scope of the disclosure as defined in the following claims.

What is claimed is:

1. A biphenyl derivative represented by the following chemical formula:

[Chemical Formula 2]

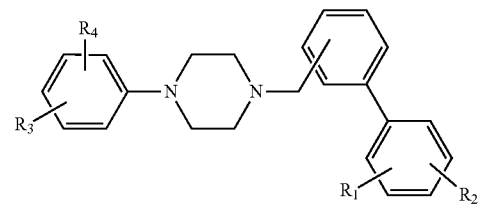

wherein
each of R$_1$ and R$_2$, which are different, is independently selected from hydrogen, halogen, alkyl, alkoxy, aryloxy and nitro; and
each of R$_3$ and R$_4$, which are different, is independently selected from hydrogen, halogen, alkyl, alkoxy, aryloxy, nitro and phenyl.

2. The biphenyl derivative according to claim 1, wherein the biphenyl derivative represented by Chemical Formula 2 has a structure of Chemical Formula 4 or Chemical Formula 5:

[Chemical Formula 4]

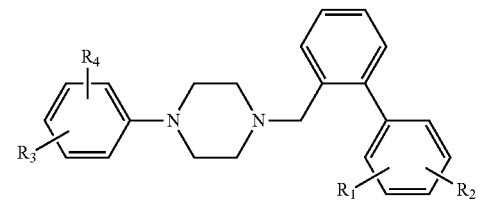

[Chemical Formula 5]

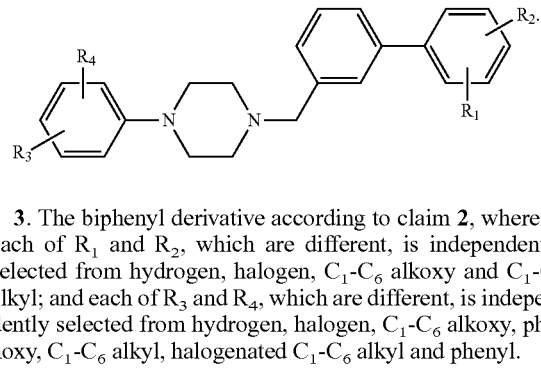

3. The biphenyl derivative according to claim 2, wherein: each of R$_1$ and R$_2$, which are different, is independently selected from hydrogen, halogen, C$_1$-C$_6$ alkoxy and C$_1$-C$_6$ alkyl; and each of R$_3$ and R$_4$, which are different, is independently selected from hydrogen, halogen, C$_1$-C$_6$ alkoxy, phenoxy, C$_1$-C$_6$ alkyl, halogenated C$_1$-C$_6$ alkyl and phenyl.

4. The biphenyl derivative according to claim 2, wherein: each of R$_1$ and R$_2$, which are different, is independently selected from hydrogen, fluoro, chloro, methyl and methoxy; and each of R$_3$ and R$_4$, which are different, is independently selected from hydrogen, fluoro, chloro, methoxy, ethoxy, isopropoxy, phenoxy, methyl and isopropyl.

5. The biphenyl derivative according to claim 2, wherein: R$_1$ is hydrogen and R$_2$ is selected from halogen, C$_1$-C$_6$ alkyl and C$_1$-C$_6$ alkoxy; and if R$_3$ is hydrogen, R$_4$ is selected from halogen, C$_1$-C$_6$ alkoxy, phenoxy, C$_1$-C$_6$ alkyl, halogenated C$_1$-C$_6$ alkyl and phenyl, or each of R$_3$ and R$_4$ is C$_1$-C$_6$ alkoxy or C$_1$-C$_6$ alkyl.

6. The biphenyl derivative according to claim 2, wherein: R$_1$ is hydrogen and R$_2$ is selected from fluoro, chloro, methyl and methoxy; and if $R_3$ is hydrogen, $R_4$ is selected from fluoro, chloro, methoxy, ethoxy, isopropoxy, phenoxy, methyl, isopropyl, and phenyl, or each of $R_3$ and $R_4$ is methoxy or methyl.

7. A method of treating a disease regulated by the action of the 5-HT$_7$ receptor selected from depression, migraine, anxiety, inflammatory pain, neuropathic pain, thermoregulatory disorder, insomnia and smooth muscle disorder, which comprises the biphenyl derivative according to claim 1 or a pharmaceutically acceptable salt thereof.

8. A method for preparing a biphenyl derivative represented by Chemical Formula 2, comprising:

preparing a biphenyl aldehyde intermediate represented by Chemical Formula 8 by Suzuki coupling an aryl boronic acid represented by Chemical Formula 6 with bromobenzene aldehyde represented by Chemical Formula 7; and preparing the compound represented by Chemical Formula 2 by reductive aminating the biphenyl aldehyde intermediate with an arylpiperazine represented by Chemical Formula 9:

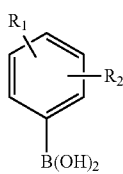

[Chemical Formula 6]

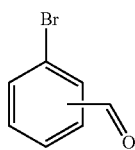

[Chemical Formula 7]

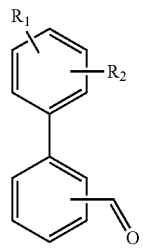

[Chemical Formula 8]

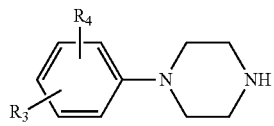

[Chemical Formula 9]

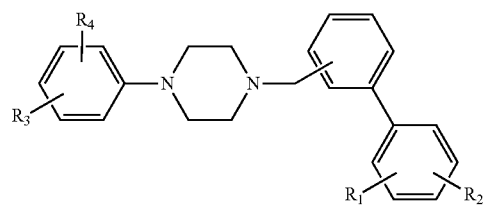

[Chemical Formula 2]

wherein
each of $R_1$ and $R_2$, which are the same or different, is independently selected from hydrogen, halogen, alkyl, alkoxy, aryloxy and nitro; and
each of $R_3$ and $R_4$, which are the same or different, is independently selected from hydrogen, halogen, alkyl, alkoxy, aryloxy, nitro and phenyl.

9. The method for preparing a biphenyl derivative represented by Chemical Formula 2 according to claim 8, wherein: $R_1$ is hydrogen and $R_2$ is selected from fluoro, chloro, methyl and methoxy; and if $R_3$ is hydrogen, $R_4$ is selected from hydrogen, fluoro, chloro, methoxy, ethoxy, isopropoxy, phenoxy, methyl, isopropyl, and phenyl, or each of $R_3$ and $R_4$ is methoxy or methyl.

* * * * *